United States Patent [19]

Yamasaki et al.

[11] Patent Number: 4,942,131
[45] Date of Patent: Jul. 17, 1990

[54] MONOCLONAL ANTIBODY AND METHOD FOR PREPARATION OF HYBRIDOMA PRODUCING SAID ANTIBODY

[75] Inventors: Masahiko Yamasaki, Hino; Kiyomi Sunaga, Kawasaki; Yoshitaka Nagai, Tokyo, all of Japan

[73] Assignee: Konica Corporation, Tokyo, Japan

[21] Appl. No.: 202,586

[22] Filed: Jun. 3, 1988

[30] Foreign Application Priority Data

Jun. 4, 1987 [JP] Japan ................................ 62-138871

[51] Int. Cl.$^5$ ...................... C12P 21/00; C12N 15/00; C12N 5/00
[52] U.S. Cl. ............................ 435/240.27; 435/70.21; 435/172.2; 530/387; 935/104
[58] Field of Search ................... 435/68, 172.7, 240.27; 530/387

[56] References Cited

PUBLICATIONS

Higashi, H, et al. Biochem, Biophys. Res. Comm. vol. 79, pp. 388–395, 1977.
Higashi, H., et al. Cancer Research, 45, pp. 3796–3802, 1985.
Miyoshi, et al., Mol. Immunol. 23, pp. 631–638, 1986.
Kaizu, et al. J. Bio. Chem. 261, pp. 11254–11258, 1986.
In: Basic & Clinical Immunology Editors: Stiles, D. P., et al, Lange Medical Publishers, Los Altos, CA., 1984 Chap. 12 pp. 152 by Theofilopoulos, A. N.
Male, et al In: Autoimmunity: Experimental & Clinical Aspects, Editors: R. S. Schwartz & N. R. Rose vol. 475 Annals of the N.Y. Acad. Sci, p. 94, 1986.
D. A. Cheresh et al., "A Monoclonal Antiody Recognizes an O-Acylated Sialic Acid in a Human Melanoma-Associated Ganglioside"J. Biol. Chem. 259: 7453–7459 (1984).
I. Miyoshi et al., "Detection of 4-O-Acetyl-N-glycolylneuraminyl lactosylceramide as One of Tumor Associated Antigens in Human Colon Cancer Tissues by Specific Antibody", Molec. Immun. 23: 631–638 (1986).

*Primary Examiner*—Christine M. Nucker
*Assistant Examiner*—Karen I. Krupen
*Attorney, Agent, or Firm*—Finnegan, Henderson, Farabow, Garrett, and Dunner

[57] ABSTRACT

Disclosed are a monoclonal antibody which recognizes specifically an O-acylsialic acid containing sugar chain and a method for preparing a hybridoma capable of producing the monoclonal antibody, which comprises using an autoimmune disease animal as the immunization animal and/or using a substance containing said sugar chain adsorbed on *Salmonella minesota* bacteria as the immunogen.

The monoclonal antibody of the present invention capable of recognizing the above described sugar chain which may be considered to be antigens related with human cancer are very useful in diagnosis of cancer.

2 Claims, 1 Drawing Sheet

MONOCLONAL ANTIBODY AND METHOD FOR PREPARATION OF HYBRIDOMA PRODUCING SAID ANTIBODY

BACKGROUND OF THE INVENTION

This invention relates to a monoclonal antibody which recognizes specifically an O-acylsialic acid containing sugar chain, particularly 4-O-acetyl-N-glycolylneuraminic lactosylceramide (hereinafter called: "GM$_3$(4-O-Ac-NeuGc)" and a method for preparing a hybridoma capable of producing said antibody.

Glycolipid is a component of cell membrane, and a diversity of molecular species exist according to the differences of the kinds, the number and the binding manner of the constituting sugars, exhibiting species specific, organ specific and cell specific distributions. It is clarified that the glycolipid functions to play an important role as concerned with control of growth or differentiation or cellular interaction, in addition to such actions as receptors for bacterial toxins, hormones, etc. and also immunological determinants such as blood group substances, etc.. Further, it is shown that with accompaniment of transformation of cells, qualitative and quantitative changes in its composition occur, whereby a part of the glycolipids can become cancer antigens, and also it is suggested that its compositional change may participate directly in the canceration mechanism, such as examples in which some glycolipids function as regulators for cell growth mechanism through growth factors and protein kinase.

On the other hand, a method for establishing cell strain producing uniform antibody having specificity for one kind of antigenic determinant was reported by Milstein et al [Nature 256, 495 (1975)], whereby it has become possible to determine qualitatively and quantitatively a minute amount of substance. For performing screening of cancer antigens, many monoclonal antibodies specific for cancer cells were prepared by use of this technique, and among them, some were clarified to be antibodies which recognize sugar chains of glycolipids or glycoproteins [J. Natl, Cancer Inst., 71, 231 (1983)].

For example, antibodies reactive with glycolipids such as GD$_2$ ganglioside or GD$_3$ ganglioside have been obtained as the monoclonal antibody to human melanoma. The monoclonal antibody NS19-9 which is specific for pancreatic cancer is reactive with glycolipids and glycoproteins having sialosyl Lewis A type sugar chain. These antibodies are useful for diagnosis and observation of therapeutical course, and also further attempted to be utilized for therapy. The qualitative and quantitative changes of glycolipids accompanied with canceration are caused by changes in activities of various glycosyl-transferases in the sugar chain biosynthesis mechanism by abnormal expression of gene, with the result that sugar chain structures which do not exist in normal tissues are produced. Such sugar chain structures can be utilized as cancer marker.

Thus, as a clue to clarification of canceration mechanism as well as a cancer antigen and a cancer marker, importance and usefulness of glycolipid are attracting attention, and its application to the clinical field such as diagnosis, therapy, etc. is expected.

Of the glycolipids, those containing, in the sugar chain, sialic acid which is an acidic sugar are comprehensively called gangliosides. Sialic acids may be broadly classified into N-acetylneuraminic acids and N-glycolylneuraminic acids, and further those having the hydroxyl groups of the respective sialic acids acylated also exist.

In recent years, it has been clarified that a complex sugar containing 9-O-acetylated N-acetylneuraminic acid functions as the receptor for Influenza C type [J. Biol. Chem., 261, 5947 (1986)]. Also, as the human cancer antigen which is recognized by the monoclonal antibody specifically reactive with human melanoma cells, GD$_3$ ganglioside O-acetylated at the 9-position of sialic acid was identified [J. Biol. Chem., 259, 7453 (1984)]. Thus, O-acylsialic acid containing chain and the antibody thereto are expected to be applied to diagnosis and therepy of various diseases including cancer.

On the other hand, while sialic acids are broadly detected in various organs, cells, body fluids of animal species, N-glycolylneuraminic acid has not yet been found in normal human being and chicken.

Heterophile antibody which is found in serum sickness patients and aggregates red blood cells of sheep, horse, pig, rabbit, guinea pig is called Hanganatziu-Deicher (hereinafer called "H-D" antibody. An antigen recognized by this antibody is called H-D antigen N-glycolylneuraminicacd containing ganglioside was reported to have H-D antigen activity [Biochem. Biophys. Res. Commun., 79, 388 (1977)], and the sugar chain structure of NeuGc α2-3 Gal was identified as the main antigenic determinant.

In recent years, an antibody reactive with various gangliosides having H-D antigen activity was prepared from the serum of a chicken immunized with N-glycolylneuraminyl lactosylceramide (hereinafter called GM$_3$(NeuGc)) which is a ganglioside having H-D antigen activity [Molec. Immun., 19, 87 (1982)]. Further, by use of this antibody, N-glycolylneuraminic acid was reported to exist characteristically in human cancer tissue [Biken J., 25, 47 (1982)]. Also, in the glycolipid extracted from human colon cancer tissue, several kinds of H-D antigen active N-glycolylneuraminic acid containing gangliosides were detected, and from among the tissues of teratoma, a glycoprotein having H-D antigen active sugar chain was detected [Gann, 75, 1025 (1984)]. When the glycolipid having H-D antigen activity detected from human colon cancer tissue by use of the antibody prepared in chicken was analyzed, GM$_3$ having O-acylated glycolyl-neuraminic acid was detected, in addition to GM$_2$(NeuGc), GM$_3$(NeuGc), IV$^3$NeuGc-nLcOse4 Cer. From the reactivity of the antibody prepared in chicken, the ganglioside was estimated to be GM$_3$(4-O-Ac-NeuGc), which is glycolyl-neuraminic acid acetylated at the 4-position. For confirmation of this fact, a polyclonal antibody which reacts with GM$_3$(1-O-Ac-NeuGc) but does not crossreact with GM$_3$(NeuGc) was prepared in chicken, and human colon cancer tissue was investigated by use of this, whereby GM$_3$(4-O-Ac-NeuGc) was surely found [Molec. Immun., 23, 631 (1986)].

Thus, some kinds of O-acylsialic acid containing sugar chains, particularly GM$_3$(4-O-Ac-NeuGc), are considered to be cancer-associated antigens, and detection thereof with high sensitivity and good precision is extremely important in cancer diagnosis. For detecting such sugar chain antigen with good efficiency, immunological assay methods are considered to be excellent in aspects of detection sensitivity and precision.

Although there is substantially no report about a polyclonal antibody to O-acylsialic acid containing sugar chain, the antibody reactive with GM3(4-O-Ac-NeuGc) was obtained in the prior art by immunizing chicken with a purified glycolipid antigen and separating from its serum [Molec. Immun., 23, 631 (1986)]. However, this method has some drawbacks. That is, (1) for obtaining antiserum, a large amount of purified antigens is required every time; (2) there are variances in affinity and activity caused primarily by individual differences between the immunized animals; (3) cumbersome operations are necessary for purification of the desired antibody, since antibodies other than the desired antibody also exist as mixed therewith; (4) the amount prepared at once is limited, etc. Therefore, for performing immunological assay correctly and with the maximum effect, it has been desired to supply a large amount of uniform antibodies of stable quality without mixing of other antibodies. Preparation of such antibodies has been already reported as the monoclonal antibody producing technique.

However, concerning monoclonal antibodies reactive specifically with O-acylsialic acid containing sugar chains and hybridomas having ability to produce said monoclonal antibodies are reported only on GD3 acetylated at the 9-position of N-acetylneuraminic acid as mentioned above, and there has been no report on a derivative having hydroxyl group other than at the 9-position substituted or hydroxyl group of N-glycolylneuraminic acid substituted.

SUMMARY OF THE INVENTION

Accordingly, the present inventors found a way to prepare a monoclonal antibody which reacts specifically with an O-acylsialic acid containing sugar chain, particularly a monoclonal antibody which reacts with GM3(4-O-Ac-NeuGc) which is a ganglioside having a N-glycolylneuraminic acid acetylated at the 4-position, in accordance with the present invention.

The present invention concerns a monoclonal antibody which recognizes specifically an O-acylsialic acid containing sugar chain and a method for preparing a hybridoma capable of producing said antibody.

Here, to recognize specifically an O-acylsialic acid containing sugar chain means to react with an O-acylsialic acid containing sugar chain and not to react with a sialic acid containing sugar chain which is not O-acylated.

The structures of the glycolipids described in the present invention are shown below:

GM3(4-O—Ac—NeuGc) [II³ Neu4AcGc—Lac Cer]

Galβ1 —→ 4Glcβ1 —→ 1Cer
3
↑
2αNeu4AcGc

GM3(NeuGc) [II³NeuGc—Lac Cer]

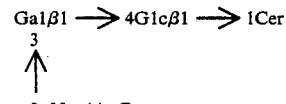

GM3(NeuAc) [II³NeuAc—LacCer]

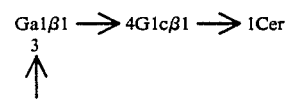

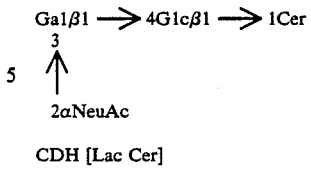

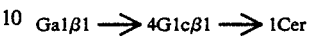

wherein Gal means galactose; Glc:glucose; GalNac:N-acetylgalactosamine; GlcNAc:N-acetylglucosamine; NeuGc:N-glycolylneuraminic acid; NeuAc:N-acetylneuraminic acid; 4-O-Ac-NeuGc and Neu4AcGc:4-O-acetyl-N-glycolylneuraminic acid; and Cer:ceramide.

Figure 1:
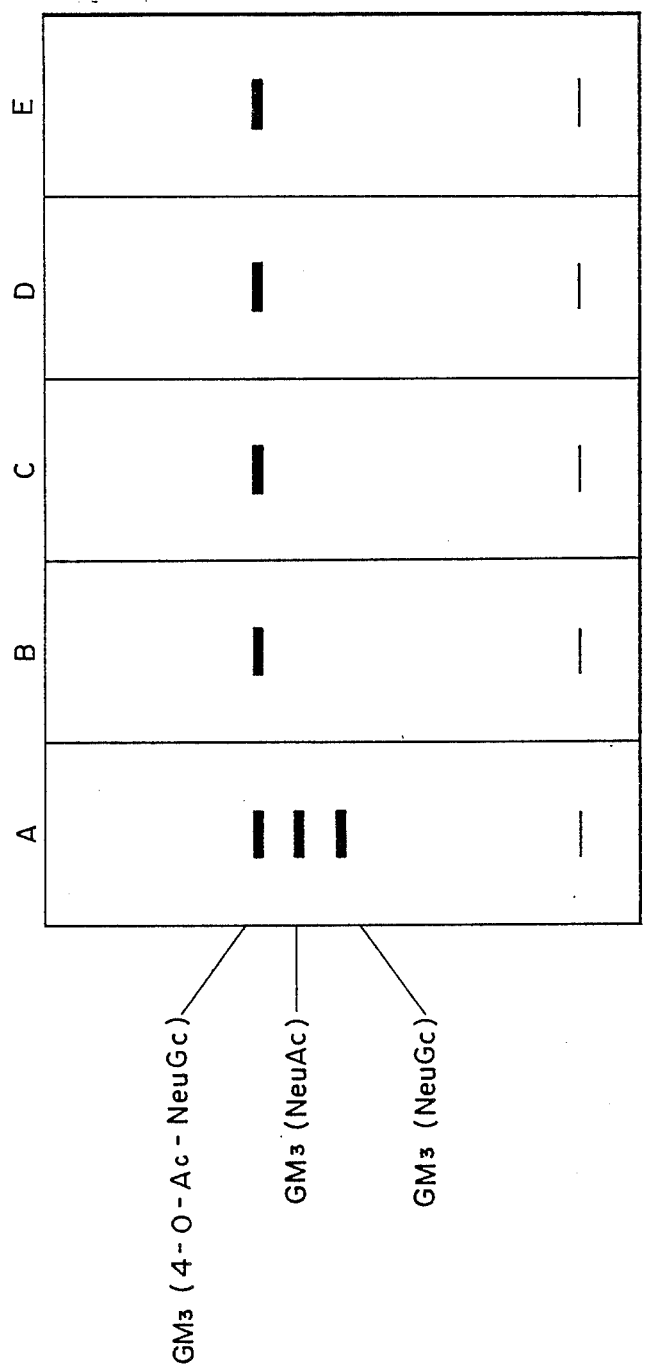
FIG. 1 shows reactivities of the monoclonal antibodies of the present invention, YHD-08, YHD-09, YHD-10 and YHD-11, with various glycolipids.

DESCRIPTION OF THE PREFERRED EMBODIMENTS:

The monoclonal antibody of the present invention has reactivity with GM3(4-O-Ac-NeuGc) which is considered to be an antigen related with human cancer, but does not react with GM3(NeuGc) having a structure which is not O-acetylated and a glycolipid containing no sialic acid.

The sugar chain structure recognized by the monoclonal antibody of the present invention may possibly exist not only in glycolipids but also in glycoproteins. Therefore, the monoclonal antibody of the present invention capable of recognizing these sugar chains which may be considered to be antigens related with human cancer are very useful in diagnosis of cancer.

The monoclonal antibody of the present invention is very useful for diagnosis of human cancer, for example, by histological or cytological examinations or blood, urine analysis or image diagnosis, and also application for therapy utilizing missile therapeutical method in which a drug is bound to the antibody or cell cytotoxicity may be possible. Further, the monoclonal antibody of the present invention is also usable for detection of the H-D antibody. Also, it is applicable for diagnosis and therapy of Marek's disease of chicken.

The monoclonal antibody of the present invention can be used as a useful tool in the basic researches about the relationship between sugar chains and the canceration mechanism, the role of sugar chains in the living body, etc.

The monoclonal antibody of the present invention may be obtained according to the method as described below.

First, a mammal is immunized with an immunogen. In this case, the mammal to be immunized should be preferably selected a view of compatibility with the myeloma cells to be used for cell fusion, and mouse or rat is more preferable. In the case of an O-caylsialic acid containing ganglioside which is the object of the present invention, particularly GM3(4-O-Ac-NeuGc), it is further preferred to use an autoimmune disease animal, particularly an autoimmune mouse. Available autoimmune disease mouse may include NZB, NZW, B/WF1, MRL/l, BXSB male, Si/Ni, etc..

Also, normal mouse of Balb/c, etc. enhanced in ability to produce autoantibody by administration of a polyclonal B cell activating agent (PBA) such as gram-negative microorganism lipid polysaccharide (LPS), dextran sulfate, etc. may be made autoimmune disease state and used as the immunized animal.

O-acylsialic acid exists in bodies of various animals including mouse.

The O-acylsialic acid containing ganglioside which is the object of the present invention may be considered to exist widely within mouse tissues, and these glycolipids are autoantigens for mouse and may be considered to be very weak in antigenicity. In the prior art method in which normal mouse such as Balb/c mouse, etc. is used as the immunized animal, it is extremely difficult to obtain a hybridoma capable of producing a monoclonal antibody to a N-glycolylneuraminic acid containing sugar chain or an O-acylsialic acid containing sugar chain. On the other hand, autoimmune disease mouse has been known to produce an antibody to an autoantigen of anti-nucleus antibody or anti-erythrocyte antibody, etc.

The present inventors have attempted to prepare a hybridoma capable of producing a monoclonal antibody to an O-acylsialic acid, particularly $GM_3$(4-O-Ac-NeuGc) and found that the desired hybridoma can be prepared very easily by immunization of an autoimmune disease mouse, to accomplish the present invention.

As the immunogen, any one of (1) the cell itself having $GM_3$(4-O-Ac-NeuGc), (2) the cell membrane component separated from said cell and (3) $GM_3$(4-O-Ac-NeuGc) separated from said cell can be used. Also, the $GM_3$(4-O-Ac-NeuGc) can be used as liposome together with phospholipid and cholesterol. Immunization may be effected according to general methods, and the above immunogen may be diluted with a phosphate buffer solution (hereinafter called "PBS"), etc. and administered intraperitoneally or intravenously. In such administration, the immunogen may be also carried on a carrier such as bovine serum albumin (BSA) or microorganism cells, etc., and also injected with an adjuvant such as Freund's adjuvant or microorganism cell adjuvant, etc. It is further preferred to administer an immunogen which is adsorbed on *Salmonella Minnesota* bacteria subjected to acetic acid treatment.

Spleen cells collected from the immunized animal are fused with mouse myeloma cells. As the myeloma cells, various known cells such as NS-1, SP-2,X63.6.5.3, P3-U1, etc. may be employed. The fusion may be carried out according to known methods. As the fusion accelerator, for example, polyethylene glycol (PEG), Sendai virus (HVJ), etc. may be employed. The ratio of spleen cells to myeloma cells used is the same as in general methods, preferably 1:1 to 10:1.

After completion of fusion, hybridoma is selected by culturing in conventional medium for selection. Since the myeloma cells as mentioned above cannot grow in HAT medium (medium containing hypoxanthine, aminopterin and thymidine), cells which can grow in HAT medium may be selected.

When the colony of hybridoma has become sufficiently large, screening and cloning of the strains producing the desired antibody are conducted.

Screening of said antibody producing strains is conducted according to the methods generally employed for detection of antibodies, such as the ELISA method [Meth. Enzymol., 70, 419 (1980)], the aggregation reaction method, the RIA method, the double immune diffusion method, etc.

Specifically, after a plate having a purified glycolipid antigen adhered thereon is blocked with BSA, it is reacted with the culture supernatant with the hybridoma to be tested, further reacted with an antibody to the mouse antibody labelled with an enzyme, and the presence of the antibody bound to said antigen is confirmed by assay of enzymatic activity to select the desired antibody producing strain.

On the other hand, cloning is conducted according to the limiting dilution method. More specifically, on a 96-well microtiter plate, hybridomas are distributed each one or less per well to have single colony grown therein. In this case, it is preferably to add mouse thymus cells as the feeder cell.

By repeating the cloning as described above, monocloned hybridoma is obtained.

The hybridoma producing the monoclonal antibody of the present invention can be stored for a long term in liquid nitrogen, and maintained in the releasable state.

For obtaining the monoclonal antibody of the present invention, there is the method in which the hybridoma is cultured in a medium and separated from the culture supernatant, or the method in which the hybridoma is administered intraperitoneally into mouse and recovered from its ascite. Further, it is possible to effect purification by use of general methods, namely ammonium sulfate precipitation, gel filtration, ion-exchange column chromatography, etc.

The present invention is described in more detail below by referring to Examples, but these Examples are not lamitative of the present invention at all.

EXAMPLE 1

(1) Isolation and purification of various glycolipids:

Horse red blood cells thoroughly washed with physiological saline were added into a large amount of cold acetone, and the precipitates obtained were subjected to successive extraction operations with respective solvent mixtures with volume ratios of chloroform:methanol:water of (10:20:1), (10:10:0) and (20:10:1). The crude glycolipids obtained were applied to a DEAE-Sephadex A-25 column chromatography to be separated into the acidic components and the neutral components, and the acidic components were subjected to Iatrobeads column chromatography to obtain $GM_3$(4-O-Ac-NeuGc) and $GM_3$(NeuGc). Similarly, from human red blood cells, CDH and $GM_3$(NeuAc) were obtained.

(2) Immunization method and cell fusion:

NZB mouse (male, 12 weeks old) was intraperitoneally injected with 300 μl of a PBS solution of $5 \times 10^8$ dead *Bordetella pertussis* bacteria, and at the same time injected intravenously with 200 μl of a PBS solution of 20 μg of $GM_3$(4-O-Ac-NeuGc) adsorbed on 80 μg of *Salmonella Minesota* bacteria. Thereafter, $GM_3$(4-O-Ac-NeuGc) adsorbed on the bacteria was similarly injected intravenously 4 times at threeweek intervals.

Three days after the final immunization, the spleen was taken out from the mouse, dissociated into single cells, and the spleen cells were washed in RPMI 1640 medium. On the other hand, mouse myeloma cells X63.6.5.3 during the logarithmic growth phase were collected and washed in RPMI 1640 medium. A suspension of $4.0 \times 10^8$ spleen cells and a suspension of $8.0 \times 10^7$ mouse myeloma were mixed together, and the medium was removed by centrifugation. Into the mixed cells was gradually added 2 ml of 50% polyethylene glycol-RPMI 1640 medium over one minute in a water bath warmed to 37° C., and stirring was conducted gently to effect fusion. 4 ml of RPMI 1640 medium was added gently with stirring over 2 minutes, and further 14 ml over 2 minutes. The medium was removed by centrifugation, and 100 ml of RPMI 1640 containing 10% fetal calf serum was added to the cells and distributed to 10 sheets of 96-well plates each in 0.1 ml per well. Next day, 0.1 ml of HAT medium (RPMI 1640 medium containing $4 \times 10^{-7}$M aminopterin, $1.6 \times 10^{-5}$ M thymidine, $1 \times 10^{-4}$M hypoxanthine, 10% fetal calf serum) was added to each well. The medium in each well was further exchanged with HAT medium in half of the amount every 3 days or 4 days. After 3 weeks, growth of hybridoma was seen in 90% of the wells.

(3) Selection of hybridoma:

Screening of the antibodies in the hybridoma culture supernatant was performed by the ELISA method. As the antigen, $GM_2$(NeuGc), $GM_3$(NeuGc) and $GM_3$(4-O-Ac-NeuGc) were employed. After 500 ng of the antigen was adsorbed on a microtiter plate for ELISA and blocked with 1% BSA-PBS solution, the culture supernatant was allowed to react therewith. Further, a peroxidase-labelled goat anti-mouse immunoglobulin antibody was reacted and the desired antibody was detected by measuring absorbance at 492 nm by use of o-phenylenediamine as the substrate. As the result, among the hybridomas prepared by immunization and cell fusion, antibodies reactive with $GM_3$(4O-Ac-NeuGc) were detected in 4 wells.

The hybridoma in which antibody activity was detected was transferred into the HT medium obtained by removing aminopterin from the HAT medium, and further transferred into RPMI 1640 medium containing 10% fetal calf serum (FCS) to be cultured therein.

The hybridoma was cloned according to the limiting dilution method. More specifically, the cells were diluted to a density of 0.8 per well in a 96-well plate and cultured together with $4 \times 10^5$/per well of mouse thymus cells, and 2 weeks later the antibody-producing cells were selected according to the ELISA method. Cloning was further repeated to obtain stable hybridomas YHD-08 (ECACC-87060301), YHD-09 (ECACC-87060302), YHD-10 (ECACC-87060303) and YHD-11 (ECACC-87060304).

The monoclonal antibodies YHD-08, YHD-09, YHD-10 and YHD-11 were all found by the ELISA method to be the class IgM.

The hybridomas YHD-08, YHD-09, YHD-10 and YHD-11 were deposited at European Collection of Animal Cell and affixed with Provisional Accession Number 87060301, 87060302; 87060303 and 87060304, respectively.

EXAMPLE 2

(1) Assay of antigenic specificity of YHD-08, YHD-09, YHD-10 and YHD-11 by the ELISA method:

With the use of 0.2 nmol of various glycolipids as the antigen, the ELISA method was practiced. The antigen adsorbed on the plate was reacted with the hybridoma culture supernatant, followed further by the reaction with a peroxidase-labelled goat anti-mouse immunoglobulin antibody. By measuring absorbance at 492 nm with o-phenylenediamine as the substrate, reactivities of the monoclonal antibody with various antigens were examined. The results are shown in the Table.

TABLE

| Glycolipid | YHD-08 | YHD-09 | YHD-10 | YHD-11 |
|---|---|---|---|---|
| $GM_3$(4-O—Ac-NeuGc) | + | + | + | + |
| $GM_3$(NeuGc) | − | − | − | − |
| $GM_3$(NeuAc) | − | − | − | − |
| CDH | − | − | − | − |

+: reactive,
−: not reactive

All of the monoclonal antibodies reacted with $GM_3$(4-O-Ac-NeuGc), i.e., N-glycolylneuraminic acid containing ganglioside, which is O-acetylated at the 4-position, but did not react with $GM_3$(NeuGc) and $GM_3$(NeuAc) which the sialic acid containing gangliosides not O-acetylated.

(2) Assay of reactivities of YHD-08, YHD-09, YHD-10 and YHD-11 on a thin layer chromatography (hereinafter called "TLC"):

Various glycolipids were spotted and developed with 5 mm width at a place 1 cm from the lower end of the TLC plate. Of the plates subjected to the same operation, one plate was color formed with orcinol reagent, and the enzyme immunostaining was effected on the other plate. That is, the antibody of the present invention was reacted, followed further by the reacton with a peroxidase-labelled goat anti-mouse immunoglobin antibody. With the use of 4-chloro-1-naphthol as the substrate, color formed spots of bluish violet were detected.

In the drawing, the results obtained by use of the three kinds of gangliosides of $GM_3$(NeuAc), $GM_3$(NeuGc) and $GM_3$(4-O-Ac-NeuGc) are shown. As the eluting solvent, chloroform:methanol:2.5N ammonia water (55:45:10 volume ratio) were employed. A shows color formation with oricinol reagent, and B, C, D and E show plates on which enzyme immunostaining is effected by use of the monoclonal antibodies of the present invention YHD-08, YHD-09, YHD-10 and YHD-11, respectively.

It can be understood that all of the monoclonal antibodies react with $GM_3$(4-O-Ac-NeuGc), but not with $GM_3$(NeuGc) and $GM_3$(NeuAc).

According to the present invention, a novel monoclonal antibody which reacts specifically with a 4-O-acetyl-N-glycolylneuraminic acid containing sugar chain and a hybridoma capable of producing said antibody can be provided. Said antibody is very effective for clarification of generation mechanism, diagnosis and therapy of cancer.

We claim:

1. A monoclonal antibody which recognizes specifically a 4-O-acetyl-N-glycolylneuraminic acid containing sugar chain, said antibody being derived from a hybridoma selected from the group consisting of YHD-08 (ECACC-87060301), YHD-09 (ECACC-87060302), YHD-10 (ECACC-87060303) and YHD-11 (ECACC-87060304).

2. A hybridoma which produces a monoclonal antibody recognizing specifically a 4-O-acetyl-N-glycolylneuraminic acid containing sugar chain, wherein said hybridoma is selected from the group consisting of YHD-08 (ECACC-87060301), YHD-09 (ECACC-87060302), YHD-10 (ECACC-87060303) and YHD-11 (ECACC-87060304).

* * * * *